US005690117A

United States Patent [19]
Gilbert

[11] Patent Number: 5,690,117
[45] Date of Patent: Nov. 25, 1997

[54] ULTRASONIC-FIBEROPTIC IMAGING VENTRICULAR CATHETER

[76] Inventor: John W. Gilbert, 898 McMeekin Pl., Lexington, Ky. 40502

[21] Appl. No.: 407,464

[22] Filed: Mar. 20, 1995

[51] Int. Cl.$^6$ .................................................. A61B 5/00
[52] U.S. Cl. ................ 128/662.06; 128/164; 128/662.05; 128/634
[58] Field of Search ............................. 604/164; 128/634, 128/662.05, 662.03, 662.06

[56] References Cited

U.S. PATENT DOCUMENTS

| | | | |
|---|---|---|---|
| 3,068,742 | 12/1962 | Hicks, Jr. et al. | 128/634 X |
| 3,556,079 | 1/1971 | Omizo | 128/662.05 |
| 4,210,029 | 7/1980 | Porter | 128/634 X |
| 4,428,379 | 1/1984 | Robbins et al. | 128/662.05 |
| 4,431,006 | 2/1984 | Trimmer et al. | 128/662.05 |
| 4,444,185 | 4/1984 | Shugar | 128/634 X |
| 4,887,606 | 12/1989 | Yock et al. | 128/662.05 |
| 4,911,170 | 3/1990 | Thomas, III et al. | 128/660.63 X |
| 5,022,399 | 6/1991 | Beigeleisen | 128/662.06 |
| 5,209,721 | 5/1993 | Wilk | 128/662.05 X |

*Primary Examiner*—Sam Rimell
*Attorney, Agent, or Firm*—Kenyon & Kenyon

[57] ABSTRACT

A rigid ultrasonic-fiberoptic stylet situated within a modified intracranial silastic catheter allows indirect and direct real time visualization through the tip of the catheter. The stylet is provided with fiberoptics and an ultrasound transducer which allows viewing through the end of the catheter. The ultrasonic portion of the stylet allows the surgeon to correctly aim the stylet and catheter towards the ventricle by giving the surgeon a 2-dimensional echogram view of the ventricle and allows the surgeon to maintain the proper trajectory or path towards the anterior horn of the lateral ventricle as the stylet and catheter are passed through the brain. The fiberoptic portion of the stylet allows the surgeon to directly view the interior of the anterior horn of lateral ventricle once the ventricle is punctured.

15 Claims, 13 Drawing Sheets

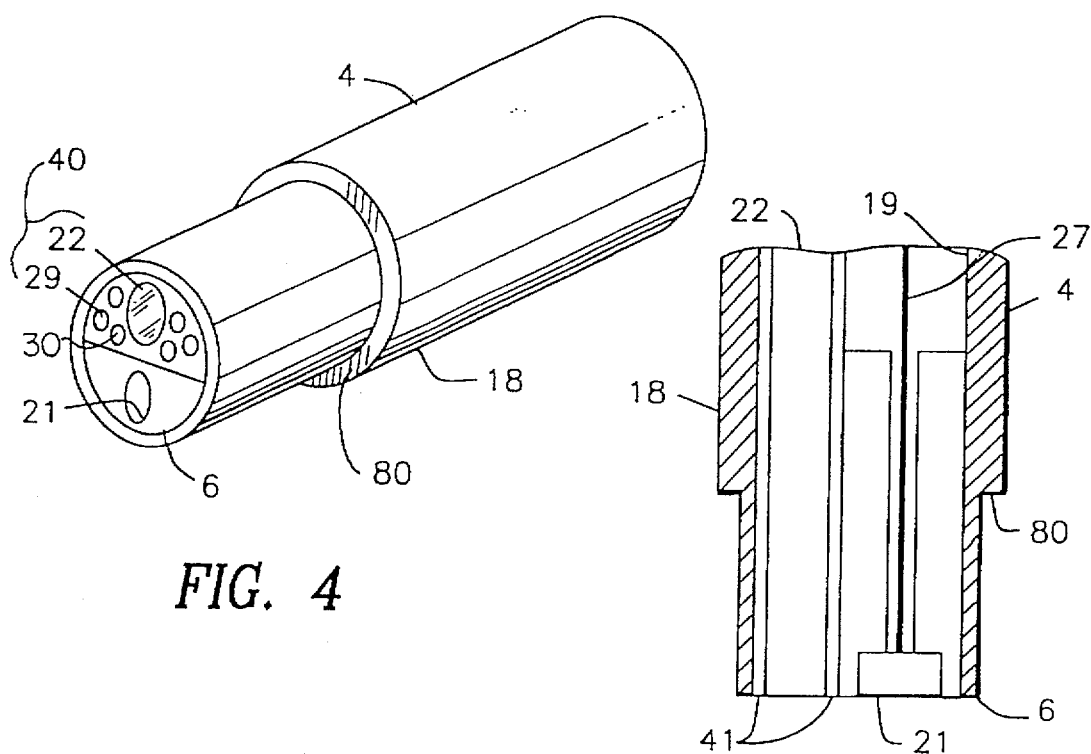
FIG. 4
FIG 4A
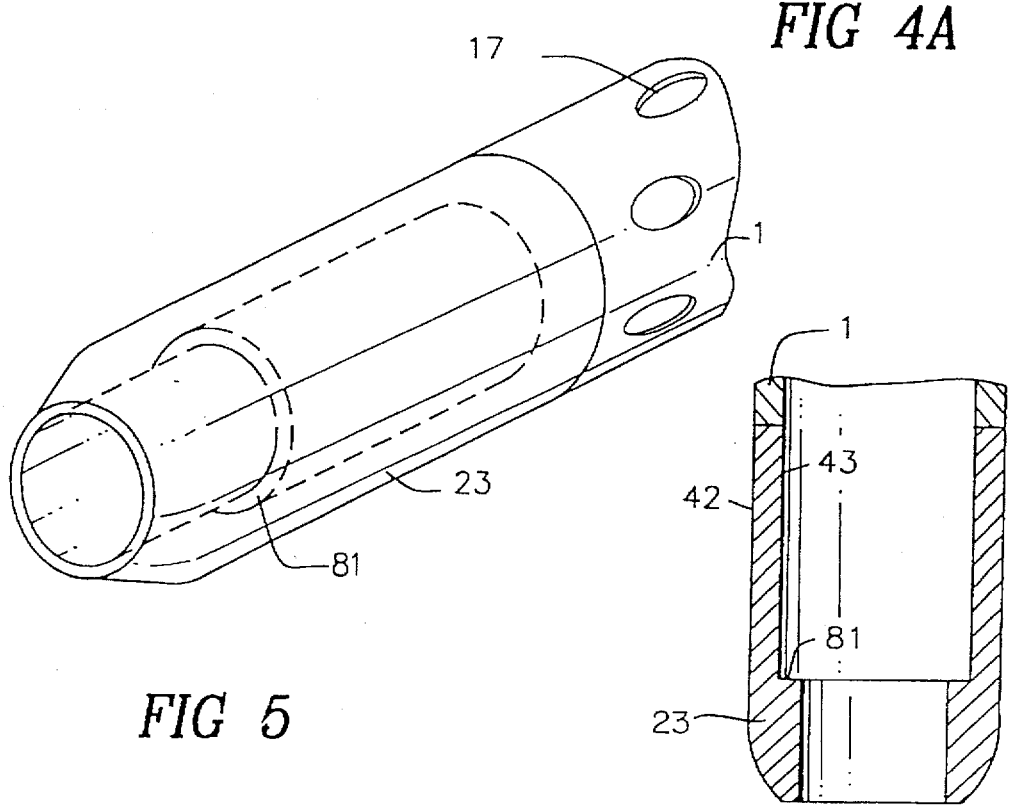
FIG 5
FIG 5A

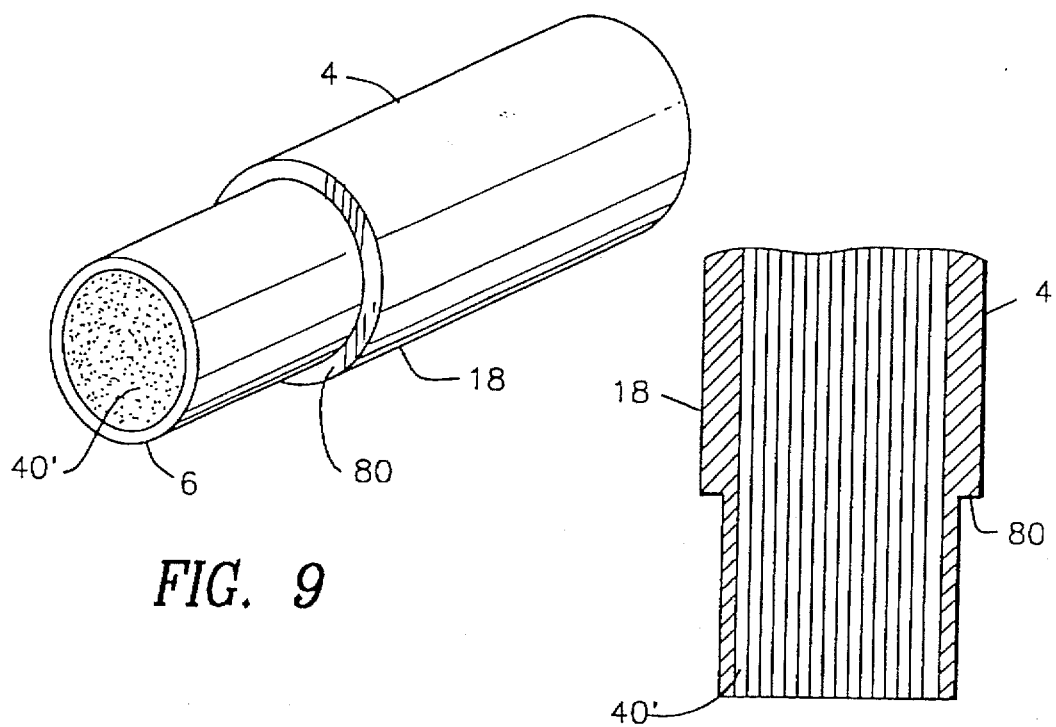
FIG. 9
FIG 9A
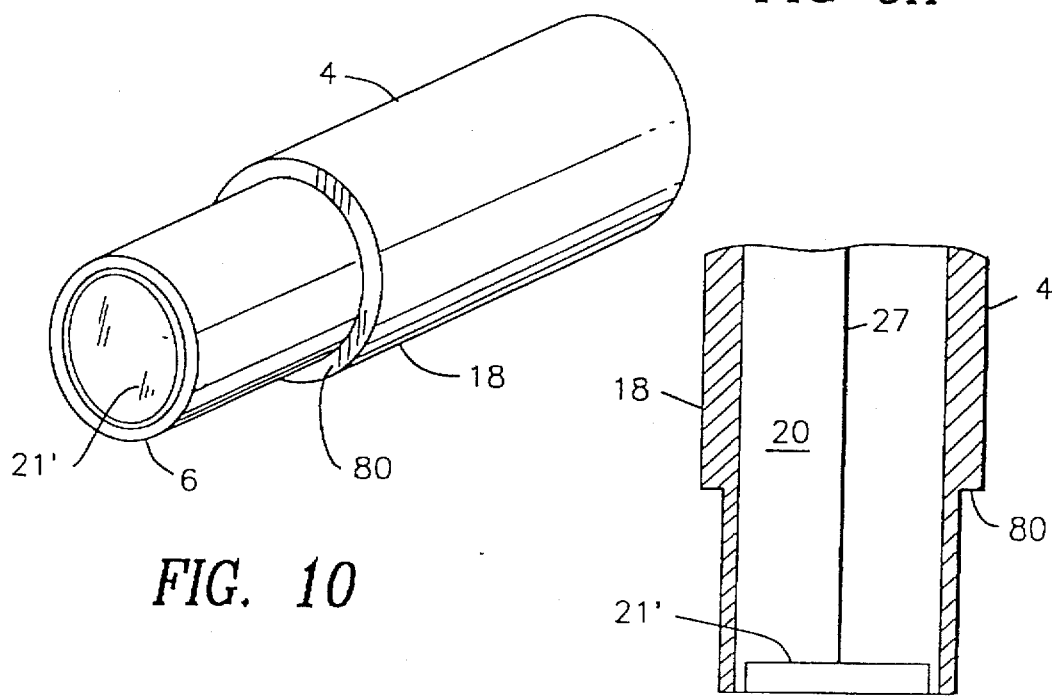
FIG. 10
FIG 10A

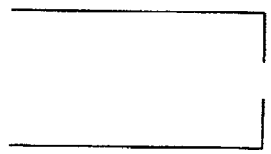
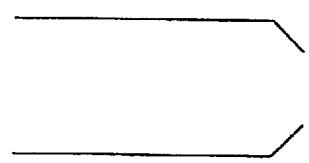
FIG. 11          FIG. 12
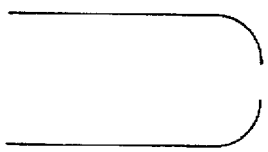
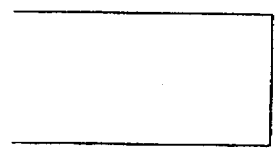
FIG. 13          FIG. 14
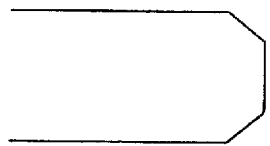
FIG. 15          FIG. 16
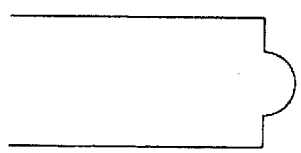
FIG. 17

ULTRASONIC-FIBEROPTIC IMAGING VENTRICULAR CATHETER

This invention relates to an apparatus and method for accurately positioning a catheter within a body cavity to be treated. More specifically, the apparatus and method of the present invention provides accurate introduction of a catheter into the ventricular system of the brain without many of the disadvantages of known technologies.

BACKGROUND OF THE INVENTION

Puncture of the lateral ventricle and placement of a flexible silastic catheter into the ventricular system is a very common procedure performed for a variety of indications including collection of cerebrospinal fluid (CSF), introduction of contrast or chemotherapy, measurement of intracranial pressure, and treatment of hydrocephalus. Conventional non-real time or "blind" techniques for placing the catheter into the ventricular system often utilize a solid rigid obturator or stylet situated within a flexible catheter. The catheter and stylet are introduced together, through, e.g., the frontal lobe or posterior occipital lobe of the brain, into the ventricle via a twist drill or burr hole made in the skull which is located by external landmarks. After the catheter is introduced into the ventricle, the stylet is removed and the distal tip of the catheter remains in the anterior horn to prevent blockage by the choroid plexus. Contrast medium or medication can then be introduced and removed and CSF can be withdrawn from the ventricular system through the catheter.

Non-real time visualization during placement of ventricular catheters has several shortcomings. One problem associated with conventional non-real time blind placement techniques is that the surgeon must guess when aiming the catheter at the target site, e.g., the ventricle, as the catheter is pushed through the brain and towards the ventricle if the aim is not correct, the catheter must be withdrawn and pushed through the brain again, at a different angle, until the ventricle is located. This may result in one or more complications. These possible complications include: 1) improper location of the distal tip of the catheter, 2) injury to neurological structures such as the fornix, thalamus, hypothalamus, or brainstem by direct penetration with the stylet and catheter or indirectly secondary to hemaroma, and 3) injury to vascular structures such as the choroid plexus. These problems can also result in increased catheter malfunction, i.e., clogging rates requiring reinsertion of another catheter. A 6.3% infection rate and 1.4% hematoma rate have been reported using intra cranial pressure (ICP) monitoring and a proximal shunt obstruction rate of approximately 1.5% has been reported using conventional insertion methods. Thus, there exists a need for an apparatus and method which allows a surgeon to accurately introduce a catheter and maintain the position of a catheter within the ventricles of the brain while reducing the likelihood of damage to the brain tissue, infection, and catheter obstruction.

SUMMARY AND OBJECTS OF THE INVENTION

The apparatus constructed in accordance with this invention utilizes a rigid ultrasonic-fiberoptic stylet situated within a modified intracranial catheter to allow indirect and direct real time visualization through the tip of the catheter. The stylet is provided with a longitudinal aperture, i.e, is hollowed out, and is packed with fiberoptics and a miniature ultrasound transducer. This ultrasonic-fiberoptic imaging stylet fits within a modified catheter which allows viewing through the end of the catheter. The ultrasonic portion of the stylet allows the surgeon to correctly aim the stylet and catheter towards the ventricle by giving the surgeon a 2-dimensional echogram view of the ventricle. This also allows the surgeon to maintain the stylet and catheter in the proper trajectory or path towards the anterior horn of the lateral ventricle as the stylet and catheter are passed through the brain. The fiberoptic portion of the stylet allows the surgeon to directly view the interior of the anterior horn of lateral ventricle once the ventricle is punctured by the stylet and catheter, thus, confirming correct placement. The fiberoptic portion also assists the surgeon in maintaining the catheter tip at the desired position during the procedure.

Ultrasound provides indirect real time acoustical visualization and is gaining in popularity with neurosurgeons. However, current probes are large and unless the patient is a baby with an open anterior fontanel the use of ultrasound requires a second large craniotomy. Thus, a forward looking miniature ultrasonic imaging transducer situated on the end of a stylet disposed in a flexible silastic catheter would allow the surgeon to correctly aim the stylet and catheter toward the ventricle through a small twist drill or burr hole in the skull.

The disposable ultrasonic-fiberoptic imaging guide or stylet situated within the modified silastic catheter with flexible cable connection to video monitors allows the surgeon to utilize previously learned techniques of "blind" ventricular puncture with the added benefit of direct and indirect real time visualization.

It is an object of this invention to provide an apparatus and method that allows a catheter to be accurately introduced into the ventricles of the brain while reducing the likelihood of brain damage.

It is another object of this invention to provide an apparatus and method that gives the surgeon real time visualization of the area to be treated.

It is yet another object of this invention to provide an apparatus and method that will prolong catheter life while reducing the likelihood that the catheter will become obstructed.

It is still another object of this invention to provide an apparatus and method for visualizing and clearing catheter obstruction.

It is a further object of this invention to provide a surgical apparatus, comprising: a catheter having a proximal end and a distal end and provided with a longitudinal bore therethrough; a stylet having a proximal end and a distal end and provided with a longitudinal bore therethrough; the stylet disposed within the longitudinal bore of the catheter; and imaging means disposed within the longitudinal bore of the stylet.

BRIEF DESCRIPTION OF THE DRAWINGS

FIG. 4 shows the stylet of FIGS. 3 and 3A provided with fiberoptic and ultrasonic imaging means in accordance with the invention;

FIG. 4A is a cross-sectional side view of FIG. 4;

FIG. 5 shows the distal tip of a catheter constructed in accordance with the invention;

FIG. 5A is a cross-sectional side view of FIG. 5;

FIG. 9 shows a distal tip of stylet constructed in accordance with an alternative embodiment of the invention;

FIG. 9A is a cross-sectional side view of the stylet shown in FIG. 9;

FIG. 10 shows the distal tip of a stylet constructed in accordance with an alternative embodiment of the invention;

FIG. 10A is a cross-sectional side view of the stylet shown in FIG. 10;

FIG. 11 shows an alternative embodiment of a catheter tip constructed in accordance with the invention;

FIG. 12 shows an alternative embodiment of a catheter tip constructed in accordance with the invention;

FIG. 13 shows an alternative embodiment of a catheter tip constructed in accordance with the invention;

FIG. 14 shows an alternative embodiment of a catheter tip constructed in accordance with the invention;

FIG. 15 shows an alternative embodiment of a catheter tip constructed in accordance with the invention;

FIG. 16 shows an alternative embodiment of a catheter tip constructed in accordance with the invention;

FIG. 17 shows an alternative embodiment of a catheter tip constructed in accordance with the invention;

DETAILED DESCRIPTION OF THE INVENTION

Figure 1:
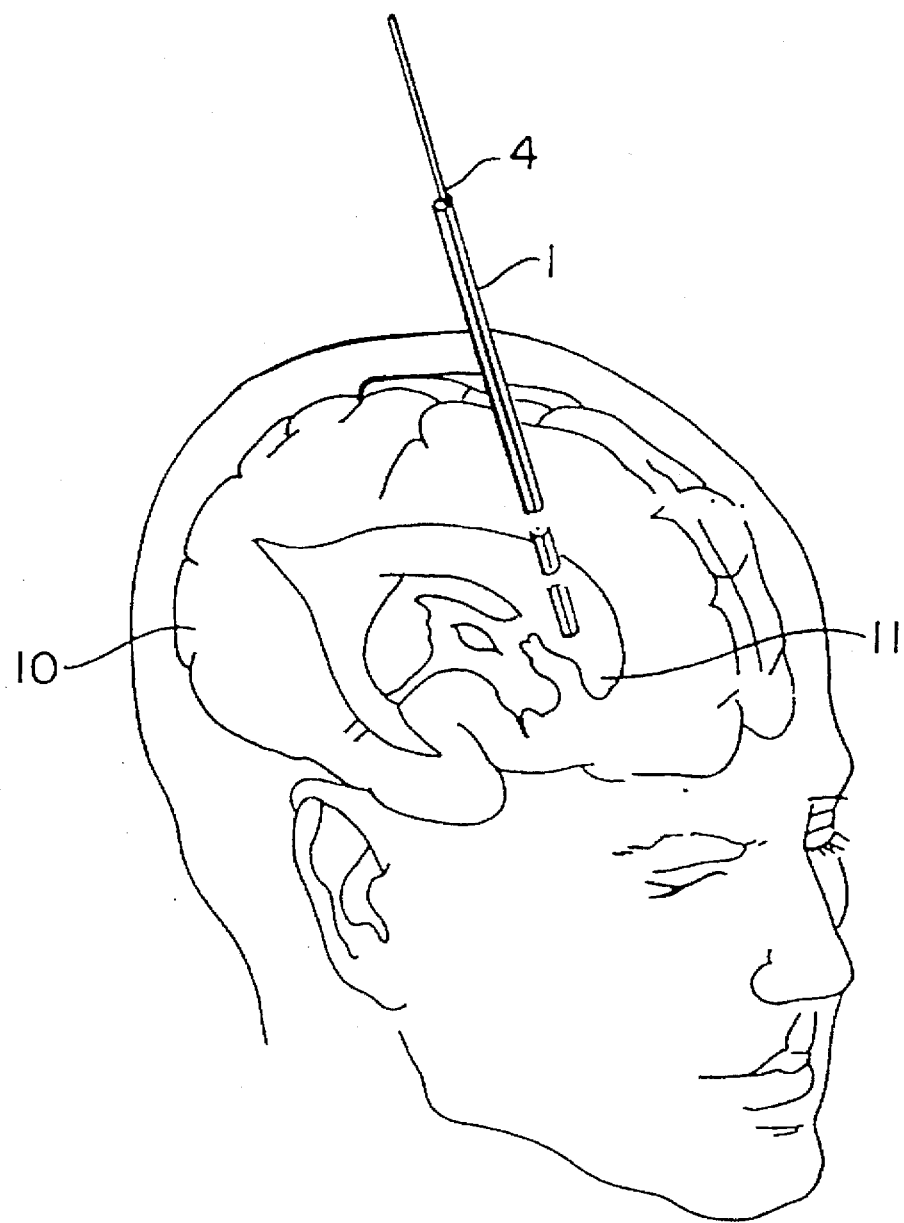
FIG. 1 shows a stylet and catheter constructed in accordance with the invention positioned in the brain.
Figure 2:
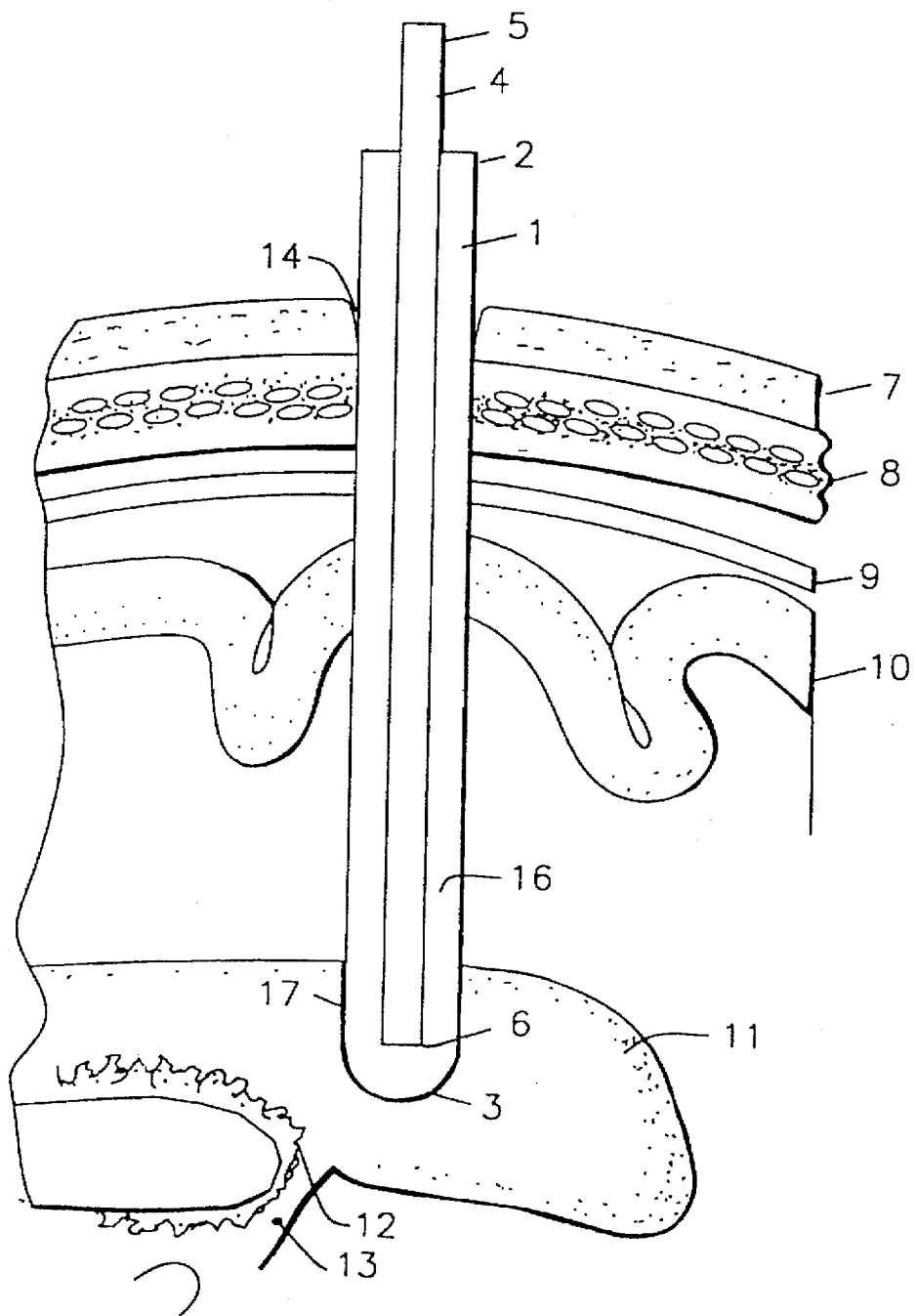
FIG. 2 is an enlarged cross-sectional side view of FIG. 1 showing a stylet and catheter constructed in accordance with the invention and positioned in the brain.

FIG. 1 shows a stylet 4 disposed in catheter 1 which has been inserted into the anterior horn of the lateral ventricle 11 of the brain 10. FIG. 2 is an enlarged cross-sectional side view of FIG. 1 and shows a stylet 4 and catheter 1 constructed in accordance with the invention which have been inserted into the anterior horn of the lateral ventricle 11 of the brain 10. The catheter 1 is provided with a proximal end 2, a distal end 3, and a longitudinal bore 16. In a preferred embodiment, the catheter 1 is flexible and silastic and is provided one or more apertures 17 at the distal end 6 which are in fluid communication with longitudinal bore 16. The distal end 3 may be provided with one or more apertures 17 in fluid communication with longitudinal bore 16. In a preferred embodiment, the ventricular catheter has a length of about 15–25 cm. In a preferred embodiment, internal longitudinal bore 16 has an internal diameter about equal to or less than about 2 mm and catheter 1 has an outside diameter about equal to or less than about 4 mm. Stylet 4 is provided with a proximal end 5, a distal end 6, and is disposed in longitudinal bore 16 of catheter 1. The catheter 1 is introduced into the brain 10 via a twist drill hole or burr 14 having a diameter of about 3 to about 5 mm which is made in the skin 7 and bone 8. The catheter 1 is then pushed through the dura 9 and brain 10 until it is positioned in the anterior horn of the lateral ventricle 11 in proximity to the choroid plexus 12 and the foramen of Monroe 13.

Figure 3:
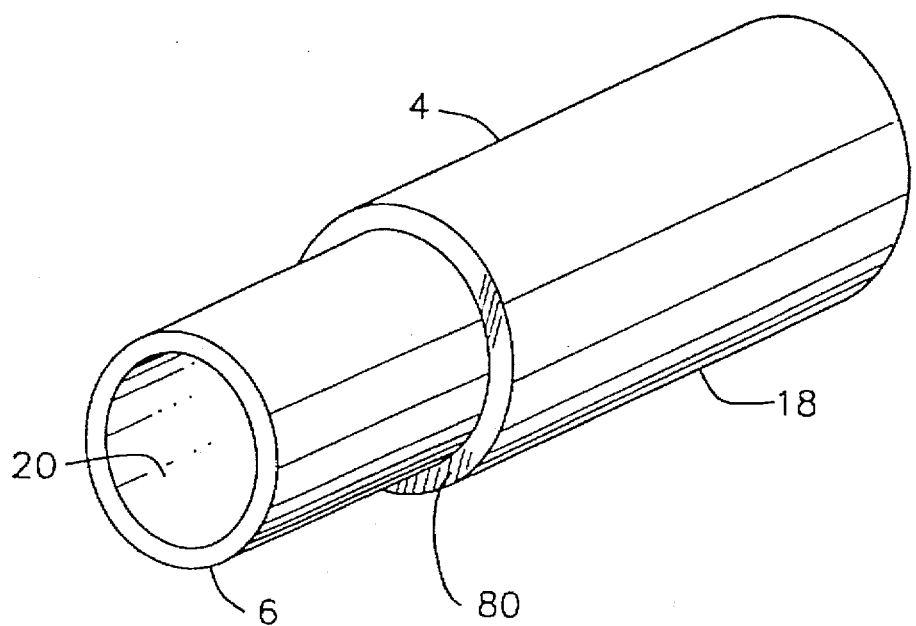
FIG. 3 shows the distal tip of a stylet constructed in accordance with the invention.
Figure 3A:
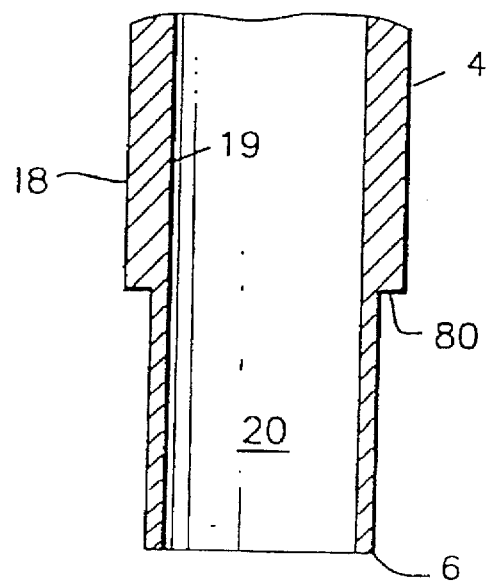
FIG. 3A is a cross-sectional side view of the stylet shown in FIG. 3.

FIG. 3 is an enlarged view of the distal end 6 of stylet 4 which is provided with an outer wall 18 and an inner wall 19 defining a stylet longitudinal bore 20. FIG. 3A is a cross-sectional side view of FIG. 3. In a preferred embodiment, the external diameter of the stylet 4 is about equal to or less than about 2 mm and the internal diameter, i.e., the diameter of longitudinal bore 20, is about 5 to about 12 mm. A securing lip 80 may be provided to limit movement of the stylet 4. The cylindrical stylet 4 approximates the tensile properties of current solid stylets but utilizes less metal and allows for symmetrical radial visualization means to be disposed in longitudinal bore 20.

Figure 7:
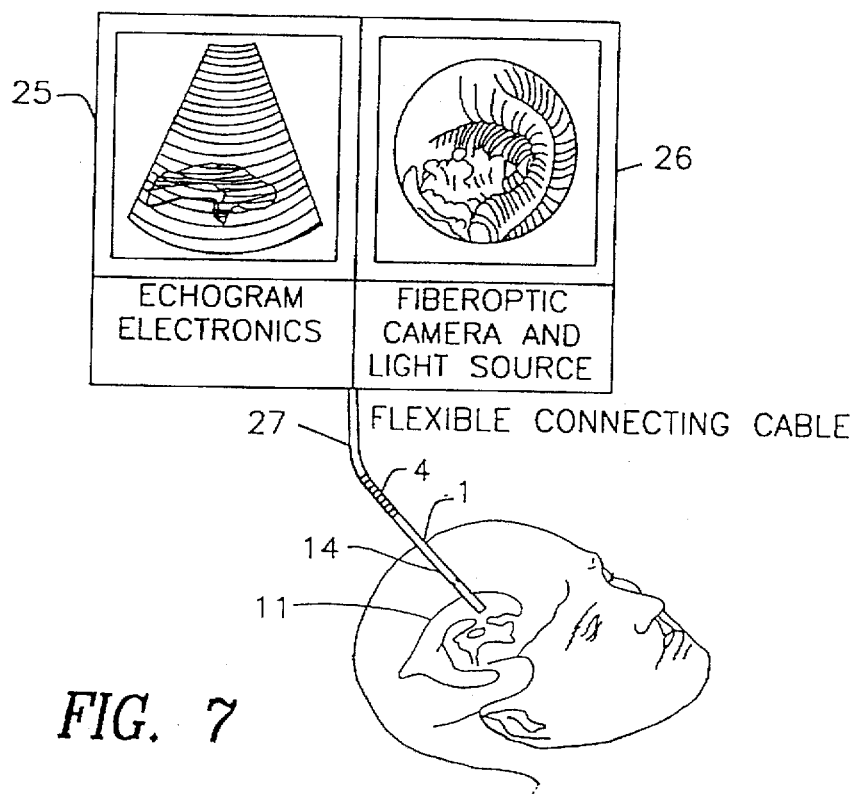
FIG. 7 shows ultrasound and fiberoptic images displayed on monitors.

FIG. 4 shows the distal end 6 of the stylet 4 shown in FIGS. 3 and 3A which is provided with an ultrasonic imaging means portion 21 to allow for the indirect imaging of the ventricle 11. This allows the surgeon to accurately choose the correct trajectory or aim before the catheter 1 is pushed through the brain 10. A variety of ultrasonic imaging means 21 well known to those skilled in the art as suitable for this purpose may be utilized, however, in a preferred embodiment a small simplified ultrasound transducer 21 consisting of a single crystal element at the tip 6 of the stylet 4 employed. The crystal element may transmit sound waves as well as receive reflected waves. By combining many small crystal elements in the circular phase compensated multi-element array technique, it is possible to obtain a miniature transducer with the advantages of a large crystal and a multi-directional beam. The ultrasound transducer 21 is connected to the ultrasound monitor and electronics by coaxial cable 27 as shown in FIG. 7.

A fiberoptic imaging means portion 40 is provided to allow for the direct imaging of the inside of the ventricle 11 and confirm correct placement of the catheter 1 in the ventricle 11. A variety of fiberoptic imaging means 40 well known to those skilled in the art as suitable for this purpose may be utilized, however, in a preferred embodiment illuminating fibers 29 and image conducting fibers 22 are employed. A concentrically-arranged layer of illuminating fibers 29 having a diameter of about 25–50 um (micron) would carry light to the field of view from a light source. An irrigation port 30 may be provided in addition to or in place of one of the illuminating fibers 29 to allow clearing of the distal optics by infusing sterile saline. The injection of 2 cc of sterile saline is commonly used to clear ventricular catheters or test cerebral compliance. The central image conducting core 22 of the fiberoptics would contain about 10,000 coherent image conducting fibers up to 10 um (micron) in diameter which transmit the image from the field of view to a camera, video monitor, and related electronics and hardware (see FIG. 7). A lens 41 (shown in FIG. 4A) covers the central image conducting core 22 to focus the image on the image conducting core 22. An individual coherent fiber transmits a picture element (pixel) or point, of an entire image. The highest resolution or number of pixels for a given image size may be obtained by using many fibers of the smallest available diameter. However, light transmission through an individual fiber decreases with increasing length of the fiber, bending of the fiber, and decreasing diameter of the fiber. Thus, the number and diameter of each individual coherent fiber dictates most of the external diameter of the catheter 1. Conventional coronary angioscopes which are relatively long, flexible, and need a very high resolution image, utilize individual image fibers with diameters of approximately 0.01 mm. This results in an overall working diameter as small as 1.5 to 2 mm. Thus, a ventricular catheter utilizing relatively short and rigid fiberoptics of suitable resolution easily permits external diameters of less than 0.5 mm. In a preferred embodiment, the total length of the fiberoptics may be about 50 to about 100 cm in order to keep the camera, light source, couplers and associated electronics and hardware remote from the patient's head and the operator's hand. This results in a lighter instrument that simulates the feel of devices used in conventional blind procedures and facilitates manipulation and control by the surgeon.

FIG. 5 shows a modified ventricular catheter 1 provided with an atraumatic, e.g., Teflon® tip 23. The tip 23 may be modified as specific applications dictate to protect the ultrasonic imaging means portion 21 and the fiberoptic imaging means portion 40 and reduce the likelihood of clogging of the catheter and trauma to the tissue. A securing ledge 81 is provided to engage securing lip 80 on stylet 4. FIGS. 11–17 show other alternative embodiments of catheter tips constructed in accordance with the invention. These tips may be constructed in a wide range of shapes and from a wide variety of materials, e.g., clear, depending upon specific applications.

Figure 6:
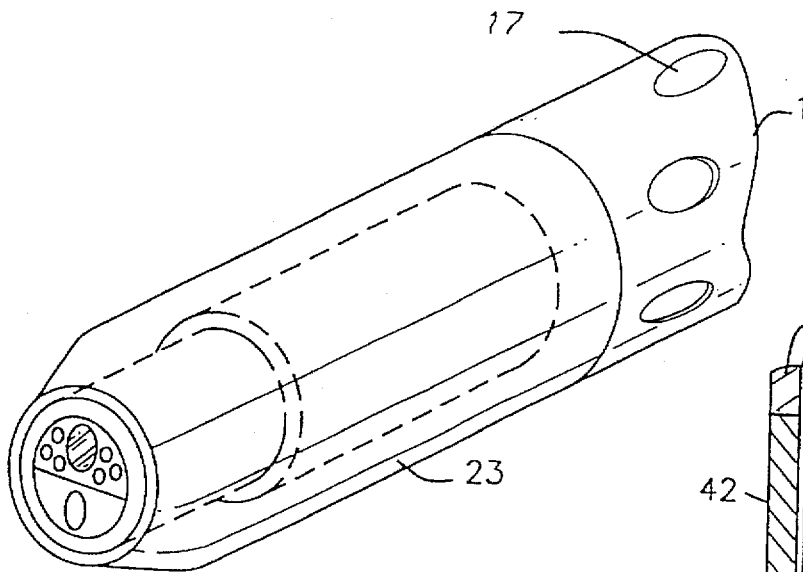
FIG. 6 shows a distal tip of a stylet seated inside the distal tip of a catheter constructed in accordance with the invention.
Figure 6A:
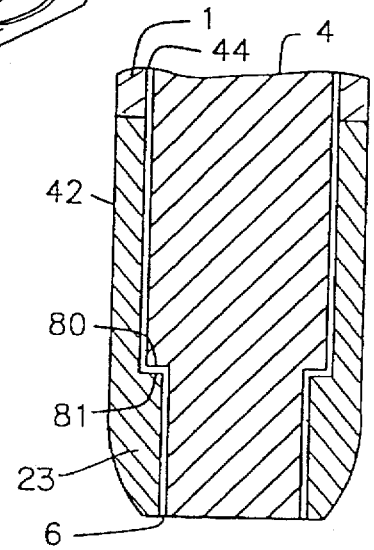
FIG. 6A is a cross-sectional side view of FIG. 6.

FIGS. 6 and 6A show a preferred embodiment in which the distal end 6 of a stylet 4 is seated inside the distal tip 3 of catheter 1. This configuration permits fiberoptic-ultrasonic imaging through the distal end 3 of the catheter 1. Securing ledge 81 engages securing lip 80 on stylet 4 and prevents the stylet 4 from extending beyond the distal end 3 of the catheter 1 during passage through the brain 10.

Figure 18:
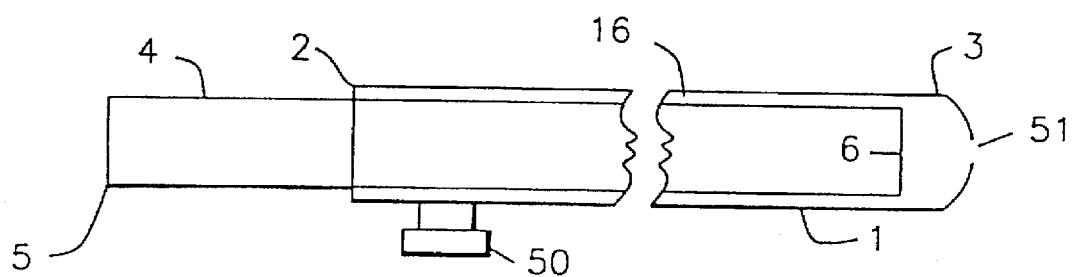
FIG. 18 shows an alternative embodiment of the invention constructed in accordance with the invention in which the stylet is adapted for selective protrusion from the tip of the catheter.
Figure 19:
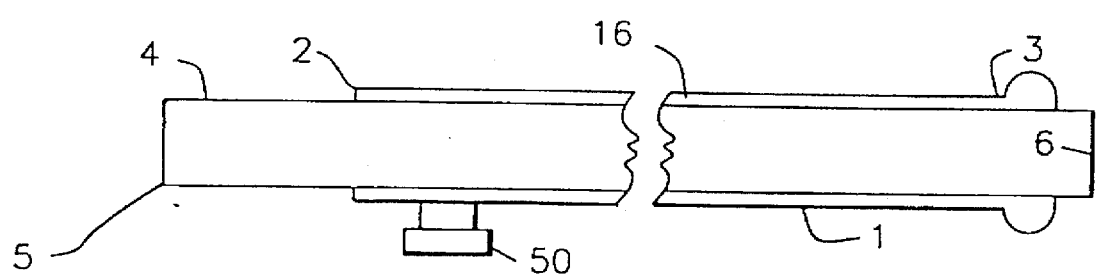
FIG. 19 shows the embodiment of the invention shown in FIG. 18 with the stylet protruding from the catheter.

In an alternative embodiment, the stylet 4 and catheter 1 are adapted so that the stylet 4 can be selectively protruded from and withdrawn into the longitudinal bore 16 of catheter 1. As shown in FIGS. 18 and 19, the catheter 1 is provided with a securing means 50 which secures stylet 4 at a predetermined position in bore 16 of catheter 1. The catheter 1 is also provided with a slit 51 at the distal end 3. In operation, the stylet 4 is inserted into bore 16 of catheter 1 so that the distal end 6 of stylet 4 does not protrude beyond the distal end 3 of catheter 1. After the catheter 1 has been positioned in the ventricle 11, as previously discussed, the surgeon releases the securing means 50, grasps the catheter 1, and pushes the stylet 4 towards the distal end 3 of catheter 1. This causes the distal end 6 of the stylet 4 to be pushed beyond the distal end 3 of the catheter 1, thus, providing the surgeon with a better view of the ventricle 11. The securing means 50 is then tightened to secure the stylet 4 at the desired position. In an especially preferred embodiment, a steering means is provided to allow the surgeon to steer or direct the distal end 6 of the stylet 4 that protrudes beyond the distal end 3 of catheter 1.

The ultrasonic imaging means portion 21 and the fiberoptic imaging means portion 40 of stylet 4 are connected by flexible fiberoptic and electrical cables to a light source, camera, video monitors, and other associated electronics related to obtaining and displaying optical and acoustical images. The fiberoptic-ultrasonic stylet 4 and the ventricular catheter 1 are introduced together into the ventricle 11 utilizing conventional procedures with the additional benefit of direct and indirect real time visualization.

As shown in FIG. 7, the ultrasound monitor 25 displays a 2-dimensional indirect image of the ventricle 11. This image is generated by the ultrasound imaging means portion 21 of the stylet 4 at the start of the procedure when the stylet 4 and catheter 1 are introduced into the twist drill hole 14 in the skull 8. The ultrasound monitor 25 allows the surgeon to accurately aim the stylet 4 and catheter 1 towards the ventricle 11 as well as maintain the correct path or trajectory during passage through the brain 10. Once the stylet 4 and catheter 1 puncture the anterior horn of the lateral ventricle 11, the fiberoptic monitor 26 displays a direct image of the interior of the ventricle 11 (foramen of monroe 13, choroid plexus 12) and confirms correct placement of the distal end 3 of the catheter 1.

Figure 8:
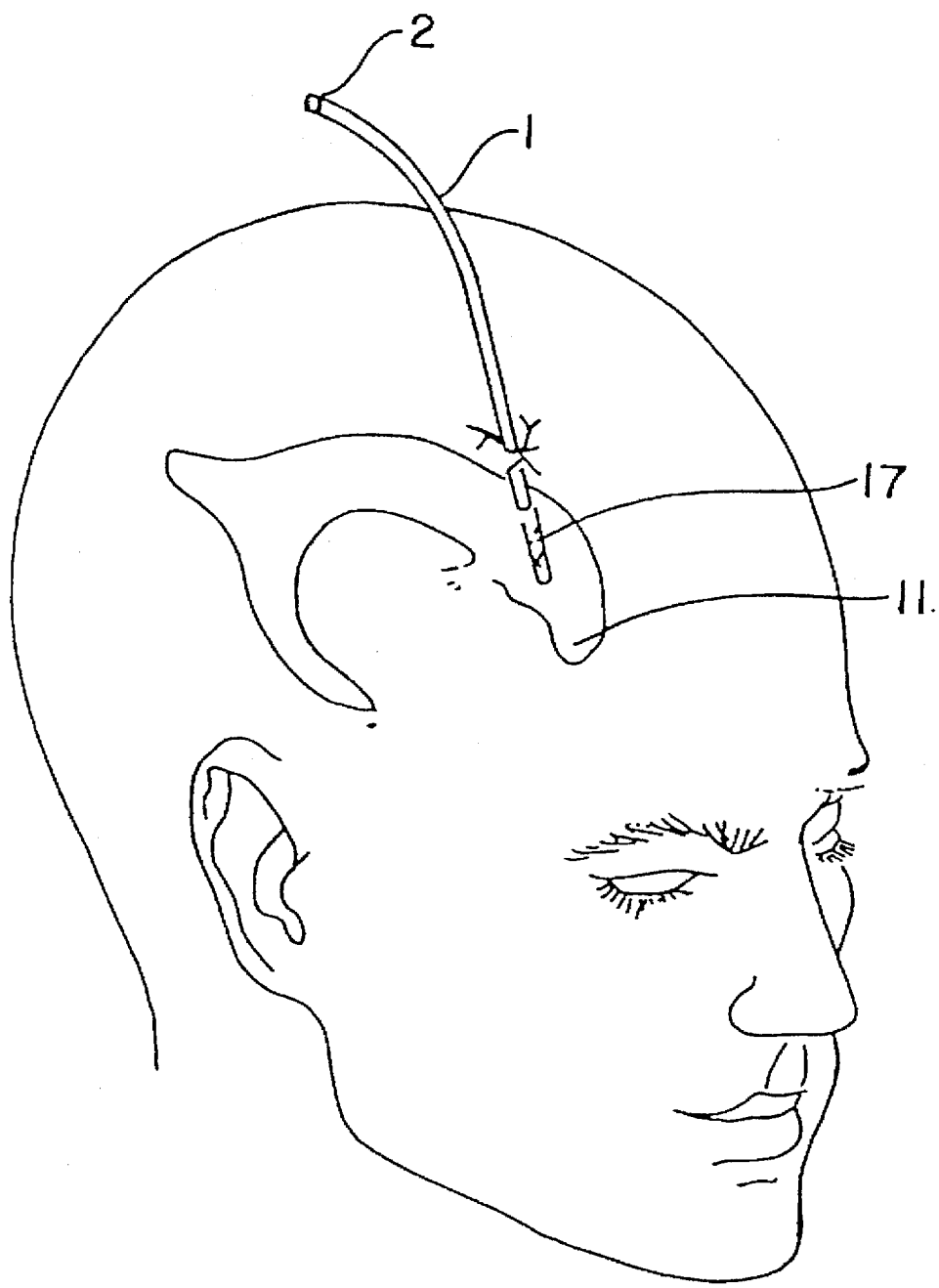
FIG. 8 shows a catheter positioned in the brain with the stylet removed.

As shown in FIG. 8, when correct placement of the catheter 1 is achieved, the catheter 1 is secured in place and the stylet 4 may then be withdrawn from the catheter 1. This allows cerebrospinal fluid (CSF) to flow from the ventricle 11 through the apertures 17 at the distal end 3 of catheter 1 into longitudinal bore 16 and towards the proximal end 2 of catheter 1. Alternatively, the stylet 4 may be sized so that if left in place CSF can flow from the distal end 3 to the proximal end 2 of the catheter 1 via the space 44 (shown in FIG. 6A) between the outer wall 18 of stylet 4 and the inner wall 43 of catheter 1.

FIGS. 9, 9A, 10, and 10A show an alternative embodiment and method of practicing the invention. FIG. 9 shows the stylet 4 of FIGS. 3 and 3A with a fiberoptic imaging means 40' disposed in longitudinal bore 20. FIG. 9A is a cross-sectional side view of FIG. 9. FIG. 10 shows the stylet 4 of FIGS. 3 and 3A with an ultrasound imaging means 21' disposed in longitudinal bore 20. FIG. 10A is a cross-sectional side view of FIG. 10.

In operation, the ultrasonic imaging means 21' is inserted into stylet 4 and the stylet 4 is inserted into the catheter 1. The ultrasonic imaging means 21' is connected to a monitor which provides the surgeon with acoustical images of the area to be penetrated as previously discussed. When the target area has been reached, the ultrasonic imaging means 21' is removed from longitudinal bore 20 of stylet 4. The fiberoptic imaging means 40' is then inserted into longitudinal bore 20 and the remainder of the procedure may be done with the physician using fiberoptic images to confirm the position of catheter 1 and maintain the position of the catheter 1 as previously discussed.

The use of video monitoring is uniquely suited for this procedure and allows surgeons to utilize previously learned skills in ventricular puncture and to maintain sterile procedures with the additional benefit of direct and indirect real-time visualization. The apparatus and method can be used for other applications such as the diagnosis and treatment of brain or spinal cysts, tumors, or fluid collections. Direct and indirect visualization will allow accurate trajectory towards the ventricle and preclude the need for X-ray confirmation of placement of the catheter tip, prevent direct injury to vital neurological structures, and instantly detect any bleeding caused by the procedure. Fewer "passes" (catheter placement attempts) as well as catheter failures will lower patient morbidity and mortality.

A convenient disposable sterile pack or kit could contain the following disposable sterile items: 1) disposable fiberoptic-ultrasonic imaging stylet, 2) modified silastic ventricle catheter, 3) plastic sleeve to place over the non-sterile flexible fiberoptic-ultrasonic connecting cables, and 4) usual ventriculostomy equipment such as twist drill, suture, etc. A mobile cart containing the video ultrasound monitor, the video fiberoptic monitor, flexible connecting cables, and associated electronics and hardware for receiving signals and for processing and displaying images, in conjunction with sterile kits would allow for bedside or intraoperative real time visualization during ventriculostomy placement.

Figure 20:
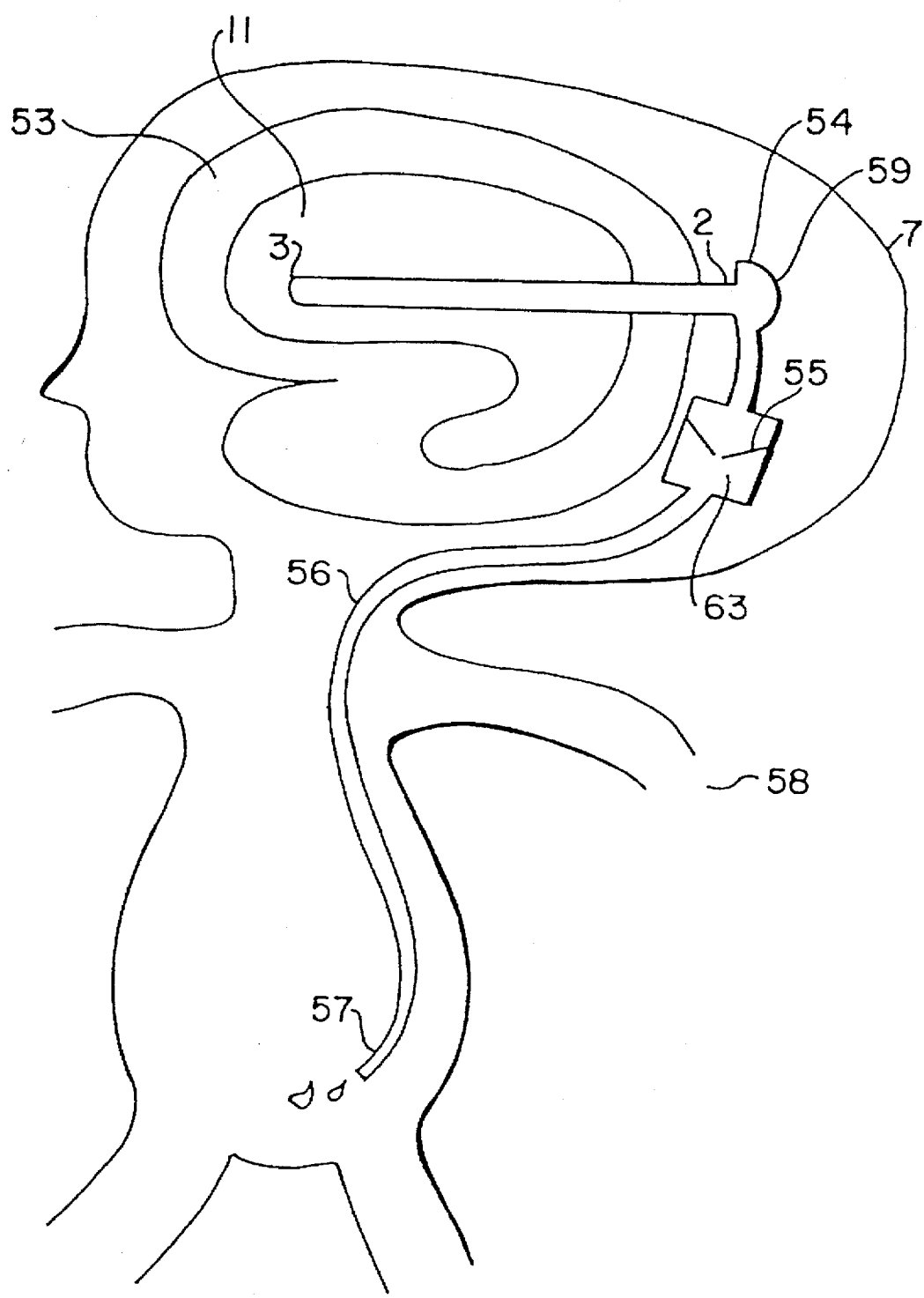
FIG. 20 shows an alternative treatment method in accordance with the invention.
Figure 21:
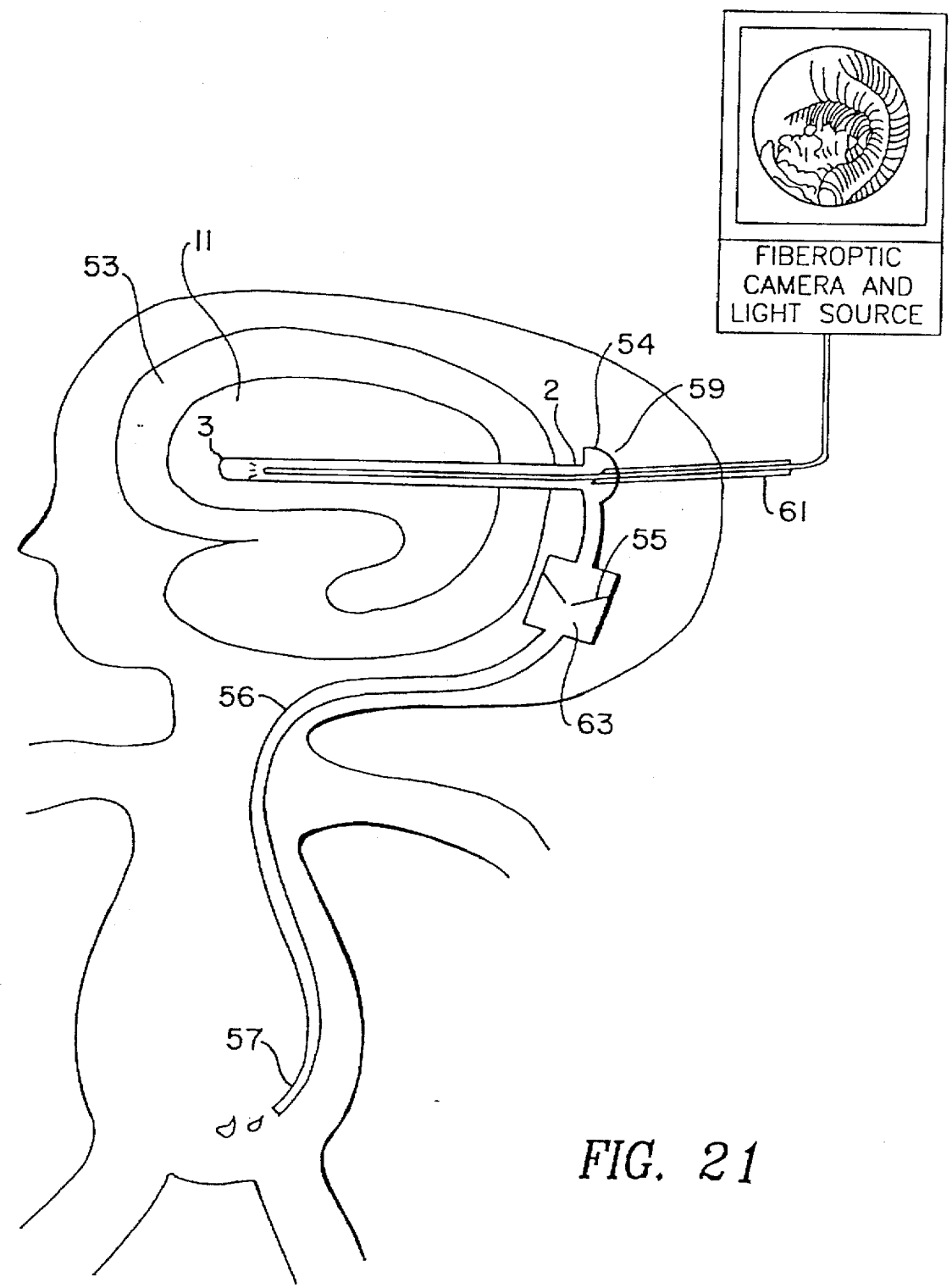
FIG. 21 shows an alternative treatment method in accordance with the invention.
Figure 22:
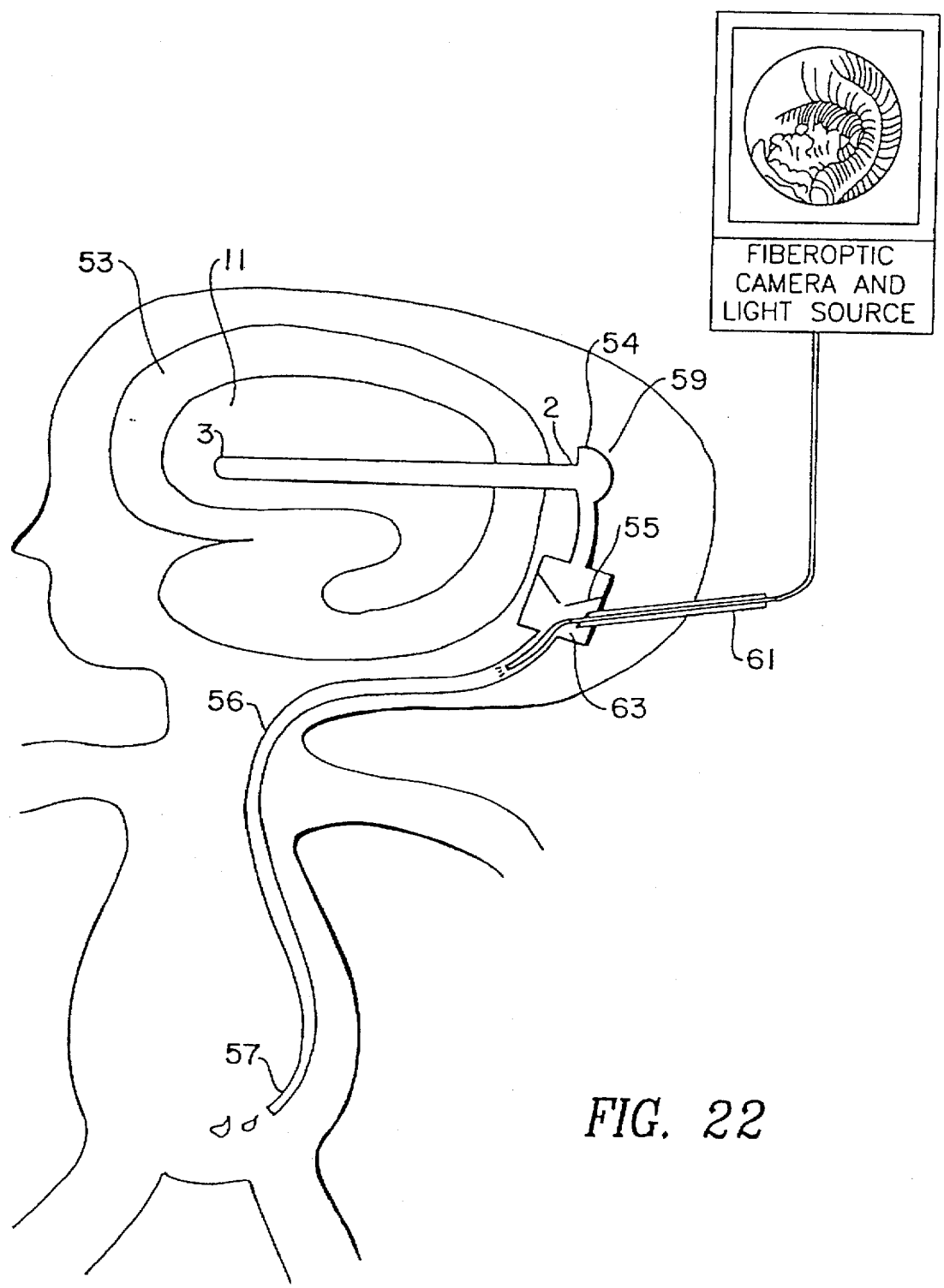
FIG. 22 shows an alternative treatment method in accordance with the invention.

FIG. 20 shows an alternative application of the invention for the treatment of hydrocephalus, an often chronic condition in which the choroid plexus 11 produces too much CSF. Conventional standard treatment involves re-routing or returning excess CSF into the patient via a ventriculoperitoneal shunt 58, a closed drainage system to prevent dehydration and to reduce the likelihood of infection. FIG. 20 shows the frontal lobe of the brain 53, frontal horn of the ventricle 11, distal end 3 and proximal end 2 of catheter 1, Rickham reservoir 54, Rickham reservoir silastic dome 59, pressure valve 55, pressure valve reservoir 63, silastic tube 56, and peritoneal catheter 57. The Rickham reservoir 54 is provided with a silastic dome 59 which can receive a needle and is self sealing when the needle is removed. In treating this condition, catheter 1 is left in the brain 10 with distal end 3 of catheter 1 disposed in the ventricle 11. As CSF is produced in the choroid plexus, the CSF passes through the apertures 17 in the distal end of catheter 1, through longitudinal bore 16 towards proximal end 2 and into the Rickham reservoir 54. When the CSF in the Rickham reservoir 54 reaches a predetermined pressure, valve 55 opens allowing CSF to flow via silastic tube 56 into the peritoneal catheter 57 which returns the CSF to the patient's abdomen. One of the complications associated with this treatment is that the ventriculoperitoneal shunt 58 may become obstructed. If this occurs, the apparatus of this invention may be used to access the ventriculoperitoneal shunt 58 and locate and clear the obstruction. In operation, as shown in FIG. 21, the skin 7 over the Rickham reservoir 54 is prepared with alcohol or betadine. A conventional stylet is placed into a conventional needle 61 and the needle 61 is inserted through the silastic dome 59 into the Rickham reservoir 54. The stylet provides the needle with rigidity and facilitates entry of the needle because the stylet provides the needle with a smoother tip during entry into the silastic dome 59. The stylet 60 is then removed and the needle 61 remains in the Rickham reservoir 54. The fiberoptic imaging means 40 can then be inserted into the bore of the needle 61 and be introduced into the ventricular catheter 1 to ascertain the nature of the blockage. Alternatively, as shown in FIG. 22, the needle 61 can be introduced into the reservoir 63 of valve 55 and the same procedure can be followed to examine the peritoneal catheter 57 for blockage. In a preferred embodiment, the fiberoptic imaging means 40 can be provided with a channel or port for receiving an apparatus for removing the obstruction, e.g., a mono-polar bovie device, laser, wire, or mechanical routing device.

Figure 23:
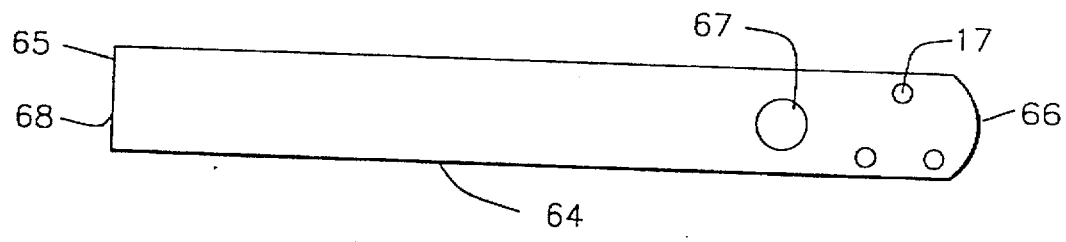
FIG. 23 shows an alternative embodiment of a catheter constructed in accordance with the invention.
Figure 24:
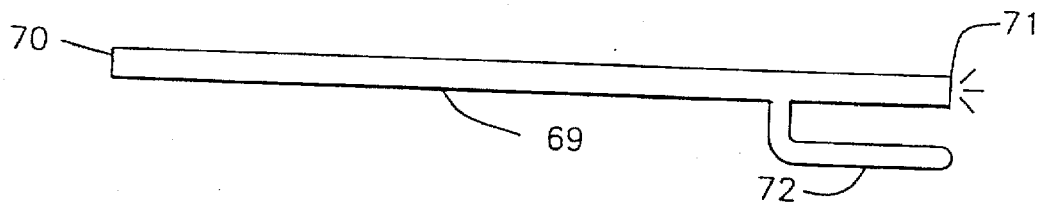
FIG. 24 shows an alternative embodiment of a stylet constructed in accordance with the invention.
Figure 25:
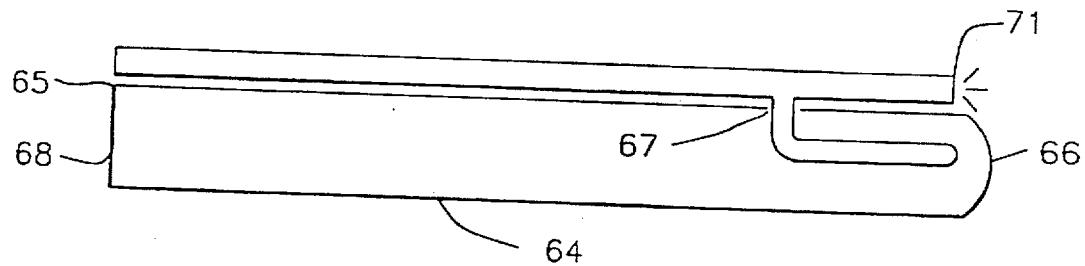
FIG. 25 shows the stylet of FIG. 24 attached to the catheter of FIG. 23.
Figure 26:
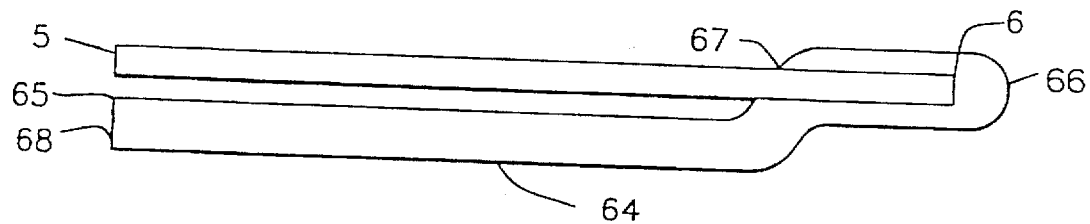
FIG. 26 shows the catheter of FIG. 23 with the stylet of FIG. 1 attached.

FIG. 23 shows an alternative embodiment of a catheter 64 constructed in accordance with the invention having a proximal end 65, a distal end 66, and longitudinal bore 68. The catheter 64 is provided with a stylet receiving aperture 67 which communicates with longitudinal bore 68. FIG. 24 shows an alternative embodiment of a stylet 69 constructed in accordance with the invention having a proximal end 70, distal end 71, and a catheter engaging means 72. As shown in FIG. 25, when catheter engaging means 72 is inserted into the stylet receiving aperture 67, the stylet 64 is retained by catheter 64. The catheter 64 and stylet 69 can then be introduced together into the patient. FIG. 26 shows the stylet of FIG. 1 disposed in the catheter of FIG. 23.

The device and method has wide applications to other common procedures such as drainage or biopsy of tumors or cysts of the brain or spinal cord that will decrease the likelihood of patient morbidity and mortality.

This invention has been described in detail with reference to particular embodiments thereof, but it will be understood that various other modifications can be effected within the spirit and scope of the invention.

I claim:

1. A surgical apparatus, comprising:
   a) a catheter having a proximal end and a distal end and provided with a longitudinal bore therethrough;
   b) a stylet having a proximal end and a distal end and provided with a longitudinal bore therethrough, said stylet sized and adapted for selective disposal within said longitudinal bore of said catheter;
   c) an ultrasonic imaging means disposed within said longitudinal bore of said stylet; and
   d) a fiberoptic imaging means disposed within said longitudinal bore of said stylet.

2. The apparatus of claim 1, further comprising an atraumatic tip disposed at said distal end of said catheter.

3. The apparatus of claim 2, wherein said distal tip of said stylet is provided with a securing lip and said atraumatic tip is provided with a securing ledge, said securing ledge adapted to engage said securing lip and secure said stylet within said longitudinal bore of said catheter.

4. The apparatus of claim 1, further comprising an irrigation port a said distal end of said stylet for irrigating said fiberoptic imaging means.

5. The apparatus of claim 1, wherein said catheter and said stylet are sized so as to provide a space between said catheter and said stylet to permit the flow of fluid between said proximal and said distal ends of said catheter via said longitudinal bore of said catheter.

6. A surgical apparatus, comprising:
   a) a catheter having a proximal end and a distal end and provided with a longitudinal bore therethrough;
   b) a stylet having a proximal end and a distal end and provided with a longitudinal bore therethrough, said stylet sized and adapted for selective disposal within said longitudinal bore of said catheter, said longitudinal bore of said stylet sized and adapted to selectively receive an ultrasonic imaging means and an optical imaging means;
   c) an ultrasonic imaging means sized and adapted for selective disposal within said longitudinal bore of said stylet; and
   d) a fiberoptic imaging means sized and adapted for selective disposal within said longitudinal bore of said stylet.

7. The apparatus of claim 6, further comprising an atraumatic tip disposed at said distal end of said catheter.

8. The apparatus of claim 7, wherein said distal tip of said stylet is provided with a securing lip and said atraumatic tip is provided with a securing ledge, said securing ledge adapted to engage said securing lip and secure said stylet within said longitudinal bore of said catheter.

9. The apparatus of claim 6, further comprising an irrigation port disposed at said distal end of said stylet for irrigating said fiberoptic imaging means.

10. A method of placing a catheter into the ventricular system, comprising the steps of:

a) constructing an apparatus comprising:
  a) a catheter having a proximal end and a distal end and provided with a longitudinal bore therethrough;
  b) a stylet having a proximal end and a distal end and provided with a longitudinal bore therethrough, said stylet sized and adapted for selective disposal within said longitudinal bore and of said catheter;
  c) an ultrasonic imaging means disposed within said longitudinal bore of said stylet; and
  d) a fiberoptic imaging means disposed within said longitudinal bore of said stylet;
 b) creating an opening in the skull;
 c) introducing said catheter into the opening in the skull;
 d) obtaining an ultrasound image of the ventricular system so as to accurately aim the catheter;
 e) introducing the catheter into the ventricular system;
 f) obtaining a fiberoptic image of the ventricular system so as to accurately position the catheter; and
 g) positioning said catheter within the ventricular system.

11. The method of claim 10, wherein said catheter and said stylet are sized so as to provide a space between said catheter and said stylet to permit the flow of fluid between said proximal and said distal ends of said catheter via said longitudinal bore of said catheter.

12. The method of claim 10, further comprising the steps of withdrawing said stylet from said catheter.

13. A method of placing a catheter into the ventricular system, comprising the steps of:

a) constructing a an apparatus comprising:
  a) a catheter having a proximal end and a distal end and provided with a longitudinal bore therethrough;
  b) a stylet having a proximal end and a distal end and provided with a longitudinal bore therethrough, said stylet sized and adapted for selective disposal within said longitudinal bore of said catheter, said longitudinal bore of said stylet sized and adapted to selectively receive an ultrasonic imaging means and an optical imaging means;
  c) an ultrasonic imaging means sized and adapted for selective disposal within said longitudinal bore of said stylet; and
  d) a fiberoptic imaging means sized and adapted for selective disposal within said longitudinal bore of said stylet;
 b) creating an opening in the skull;
 c) disposing said ultrasound imaging means in said longitudinal bore of said stylet;
 d) disposing said stylet within said longitudinal bore of said catheter;
 e) introducing said catheter into the opening in the skull;
 f) obtaining an ultrasound image of the ventricular system so as to accurately aim the catheter;
 g) introducing the catheter into the ventricular system;
 h) removing said ultrasound imaging means from said longitudinal bore of said stylet;
 i) introducing said fiberoptic imaging means into said longitudinal bore of said stylet;
 f) obtaining a fiberoptic image of the ventricular system so as to accurately position the catheter; and
 g) positioning said catheter within the ventricular system.

14. The method of claim 13, wherein said catheter and said stylet are sized so as to provide a space between said catheter and said stylet to permit the flow of fluid between said proximal and said distal ends of said catheter via said longitudinal bore of said catheter.

15. The method of claim 13, further comprising the step of removing said optical imaging means from said longitudinal bore of said stylet.

* * * * *